United States Patent [19]

Uphold et al.

[11] Patent Number: 4,763,663

[45] Date of Patent: * Aug. 16, 1988

[54] ESOPHAGEAL STETHOSCOPE AND VITAL SIGNS MONITOR SYSTEM

[75] Inventors: James D. Uphold, Canoga Park; Robert L. Pfohl, Anaheim Hills, both of Calif.

[73] Assignee: Vitacomm, Ltd., Anaheim, Calif.

[*] Notice: The portion of the term of this patent subsequent to Oct. 28, 2003 has been disclaimed.

[21] Appl. No.: 924,047

[22] Filed: Oct. 28, 1986

Related U.S. Application Data

[63] Continuation of Ser. No. 522,640, Aug. 11, 1983, Pat. No. 4,619,268.

[51] Int. Cl.⁴ .............................................. A61B 5/02
[52] U.S. Cl. ................................. 128/671; 128/736; 128/715
[58] Field of Search ............... 128/660, 671, 736, 664, 128/804, 903, 715, 773

[56] References Cited

U.S. PATENT DOCUMENTS

| | | | |
|---|---|---|---|
| 2,729,211 | 1/1956 | Peter | 128/2.1 |
| 3,405,288 | 10/1968 | Dittrich | 128/715 |
| 3,488,586 | 1/1970 | Watrous et al. | 324/96 |
| 3,951,136 | 4/1976 | Wall | 128/2.06 |
| 4,038,976 | 8/1977 | Hardy et al. | 128/903 |
| 4,129,125 | 12/1978 | Lester et al. | 128/2.05 |
| 4,176,660 | 12/1979 | Mylrea et al. | 128/671 |
| 4,237,900 | 12/1980 | Schulman et al. | 128/736 |
| 4,248,241 | 2/1981 | Tacchi | 128/671 |
| 4,301,809 | 11/1981 | Pinchak | 128/695 |
| 4,304,239 | 12/1981 | Perlin | 128/642 |
| 4,304,240 | 12/1981 | Perlin | 128/671 |
| 4,312,358 | 1/1982 | Barney | 128/736 |
| 4,331,156 | 5/1982 | Apple et al. | 128/715 |
| 4,349,031 | 9/1982 | Perlin | 128/642 |
| 4,361,153 | 11/1982 | Slocum et al. | 128/903 X |
| 4,362,164 | 12/1982 | Little et al. | 128/715 |
| 4,362,166 | 12/1982 | Furler et al. | 128/670 |
| 4,369,794 | 1/1983 | Furler | 128/671 |
| 4,383,534 | 5/1983 | Peters | 128/715 |
| 4,475,555 | 10/1984 | Linder | 128/670 |
| 4,484,583 | 11/1984 | Graham | 128/715 |

FOREIGN PATENT DOCUMENTS

| | | | |
|---|---|---|---|
| 1131315 | 9/1982 | Canada | 128/903 |
| 2003138 | 7/1971 | Fed. Rep. of Germany . | |
| 2823931 | 11/1979 | Fed. Rep. of Germany . | |

OTHER PUBLICATIONS

Linnarsson et al, "Oesophageal Probe . . . ", Med & Biol. Eng & Comp., 1982.

Primary Examiner—Edward M. Coven
Attorney, Agent, or Firm—Baker, Maxham & Jester

[57] ABSTRACT

A patient vital signs monitoring system includes an elongated flexible esophageal stethoscope catheter including a microphone and a thermister measuring means detachably connected to a processing monitor through a patient interface unit for electrical isolation of the patient from the processing system to assure patient safety from electrical currents. a single microphone, including an amplifier, picks up and transmits sound from the stethoscope catheter through a processing system including an audio filter system in the patient interface unit which amplifies the heartbeat and breathing sounds and transmits signals to the monitor/transmitter unit through a fiberoptic link to the microprocessor where the signals are compared against reference limits for generating alarm signals in response to critical deviations from preset norm. The monitor/transmitter unit is programmed to be self-monitoring prior to going into the normal patient monitoring mode and while in the monitoring mode. An IR transmitter in the monitor/transmitter unit transmits the vital breath and heart sounds by way of an infrared signal which is received by a portable receiver carried by the operator and monitored by an earphone to eliminate interference from electrical systems and avoiding additional hardline electrical connections within the operating room.

20 Claims, 5 Drawing Sheets

ESOPHAGEAL STETHOSCOPE AND VITAL SIGNS MONITOR SYSTEM

REFERENCE TO RELATED APPLICATION

This application is a continuation of our co-pending application Ser. No. 522,640, filed Aug. 11, 1983, entitled "Esophageal Stethoscope and Vital Signs Monitor System", now U.S. Pat. No. 4,619,268, granted Oct. 28, 1986.

BACKGROUND OF THE INVENTION

The present invention relates to medical instrumentation and pertains particularly to an electronic monitoring system for monitoring patient vital signs during and following an operation.

Esophageal stethoscopes are currently employed by most anesthesiologists during general anesthesia requiring endotracheal intubation. The stethoscopes currently used are of a hollow, flexible tubular construction with distal ends perforated and covered by pliable balloons. Sound is conducted by way of the air column within the tube and then by additional tubing to the anesthesiologist's ear. These esophageal stethoscopes in theory provide a constant audible monitor of breath and cardiac sound which is interpreted by the anesthesiologist. In practice, however, sound transmission characteristics vary with the physical characteristics of the tubing and can be further modified by sounds from outside the patient and by fit of the ear piece. Often cardiac sounds are overwhelmed by breath sounds making it difficult for the anesthesiologist to accurately monitor and interpret the vital signs. The prior art stethoscope also necessitates a tethering of the anesthesiologists's era to the patent which sometimes may actually preclude its use in some circumstances.

It is desirable that improved vital sign monitoring means be available which is also less inhibiting to the mobility of the anesthesiologist.

SUMMARY AND OBJECTS OF THE INVENTION

It is the primary object of the present invention to provide an improved vital signs monitoring system for a living being.

In accordance with the primary aspect of the present invention, a vital signs monitoring system includes an esophageal stethoscope catheter incorporating a miniature microphone for electrical pickup and transmission of signals respresentative of the sounds generated within the chest of a patient. Processing circuits enable separation of the breath from heart sounds as desired by the operator and enable measurement of heart (pulse) and breath (respiration) rates and comparison of the measured rates with preset reference rates and initiate a visual or audible signal in response to a critical variation from the norm. Similarly, the temperature is monitored and compared to a preset norm with a visual or audible signal given in response to abnormal deviation from the norm. The system includes electrical isolation means isolating the patient interface module to which the esophageal stethoscope catheter is attached and communicates the data via fiberoptics to the monitor/transmitter unit for isolation of electrtical systems from the patient. Vital sound data are encoded for transmission via IR energy to an IR receiver and ear piece which can be worn by the anesthesiologist to permit maximum mobility thereof. A self-destruct circuit destroys the esophageal catheter microphone to prevent reuse of possible damaged or ineffective probes which may result from attempted resterilization.

BRIEF DESCRIPTION OF THE DRAWINGS

The above and other objects and advantages of the present invention will become apparent from the following description when read in conjunction with the drawings wherein:

FIG. 7 is a schematic illustration of the electronic circuit for the catheter and patient interface unit.

DETAILED DESCRIPTION OF A PREFERRED EMBODIMENT

Figure 1:
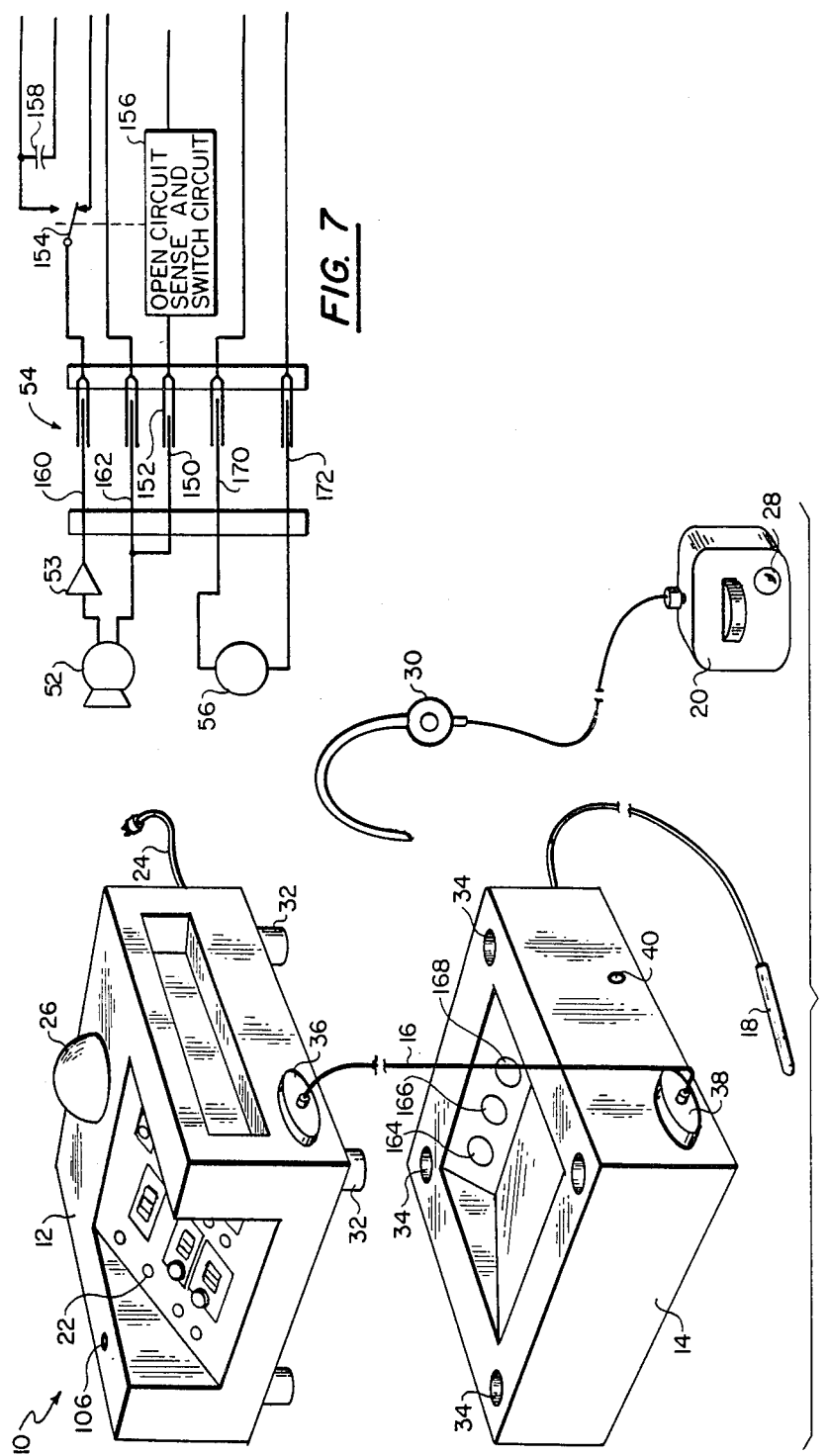
FIG. 1 is a perspective view of the system in accordance with the invention.

Referring to FIG. 1 of the drawings, a system in accordance with the invention is illustrated and designated generally by the numeral 10. This system comprises a monitor/transmitter unit 12 which contains a microprocessor, the main control and displays panel, and main alarm indicator system. This monitor/transmitter unit is connected to a patient interface unit 14 which is battery powered by a low voltage battery in order to eliminate the threat of any possible patient electrical burn, etc. The interconnection between the monitor/transmitter unit 12 and the patient interface unit 14 is by way of a fiberoptic cable 16 for electrical isolation of the units. The esophageal stethoscope catheter unit 18 is detachably connected to the patient interface unit 14 which contains minor electronics controls as well as a trigger destruct for destroying the catheter microphone amplifier circuit. The units 12 and 14 are housed in appropriate cabinets such as illustrated for modular stacking for reasons as will be described and for ease of transport in a carrying case.

A receiver/ear piece 20 in the form of an infrared radiation receiver 20 including an earphone enables the anesthesiologist to be completely mobile and monitor the vital sounds within the patient's chest. The vital sounds information is transmitted by an infrared transmitter from the monitor/transmitter unit 12 which avoids interference from other electrical systems.

The monitor/transmitter unit 12 is housed in a generally box-like housing having a generally square box-like configuration with a sloped main control and display panel 22 disposed at approximately 30 degrees to the horizontal for ease of access. the monitor/transmitter unit is powered such as by line cord 24 to electrical outlet which supplies electrical power from a suitable source such as 110 or 120 volts. A charger system of conventional construction which keeps charged at least two rechargeable batteries or power packs to enable operation of the battery power receiver/ear piece 20 is included in the monitor/transmitter unit.

The monitor/transmitter unit includes an infrared transmitter transmitting data regarding heart and breath sounds through an omni-directional infrared antenna 26 which infrared signals are received by the remote infrared receiver/ear piece 20 by its infrared receiver 28. The antenna 26 as illustrated has a hemispherical configuration and transmits the IR signals outward in all directions from that point so that it can be received anywhere within the operating room. The infrared carrier signal, because of its frequency range, provides for clear channel reception the presence of radio frequency interference and electro-magnetic interference and is also room or space confined. The remote receiver/ear piece 20 is battery-powered and housed within a small housing that can be either cdlipped to a uniform. An earphone or plug 30 including an ear clip is connected by a suitable cable to the receiver unit 20.

The monitor/transmitter unit 12 is designed to stack with the patient interface unti 14 with the monitor/transmitter unit housing including a plurality of support legs 32 adapted to extend into depressions or receptacles 34 on the upper surface of the generally box-like housing of the patient interface unit 14. These housings are constructed of any suitable material such as a high-impact plastic for appropriate durability and maintenance.

The fiberoptics interconnection or cable 16 between the monitor/transmitter unit 12 and the patient interface unit 14 is connected by disconnect couplers 36 and 38 enabling the units to be disconnected such that the patient interface unit may be transported with the patient from the operating room to a post-operative care unit with the esophageal stethoscope catheter remaining in place in the patient. A suitable jack 40 is provided for enabling head phone or ear plug connection to permit continuous monitoring during transport of the patient from operating room to post-operative care unit. The patient interface unit is self-contained with its own low voltage battery and separate controls including an on-off switch 164, volume control 166 and battery condition indicator 168.

The monitor system in accordance with the invention includes four main subassemblies comprising a catheter assembly, a patient interface unit, monitor/transmitter unit, and a receiver/ear piece assembly. The patient interface unit comprises a low powered analog signal processing circuitry with a standard analog to digital signal converter and a battery power supply. The battery power supply preferably includes alternate rechargeable batteries. The signal output from the analog to digital converter is converted into light signal format by means of a conventional fiberoptic coupler 62 and transmitted by a fiberoptic cable 16 to the monitor/transmitter unit 122. Thus, the patient is entirely electrically isolated from either ground or line power electrical potential by means of this mechanization.

The monitor/transmitter unit includes a conventional microprocessor, infrared transmitter, circuitry for electrical interfacing with the patient interface unit and the system control panel. The control panel contains the basic functional controls for controlling the various functions and operations of the system to be more fully described later.

Figure 3:
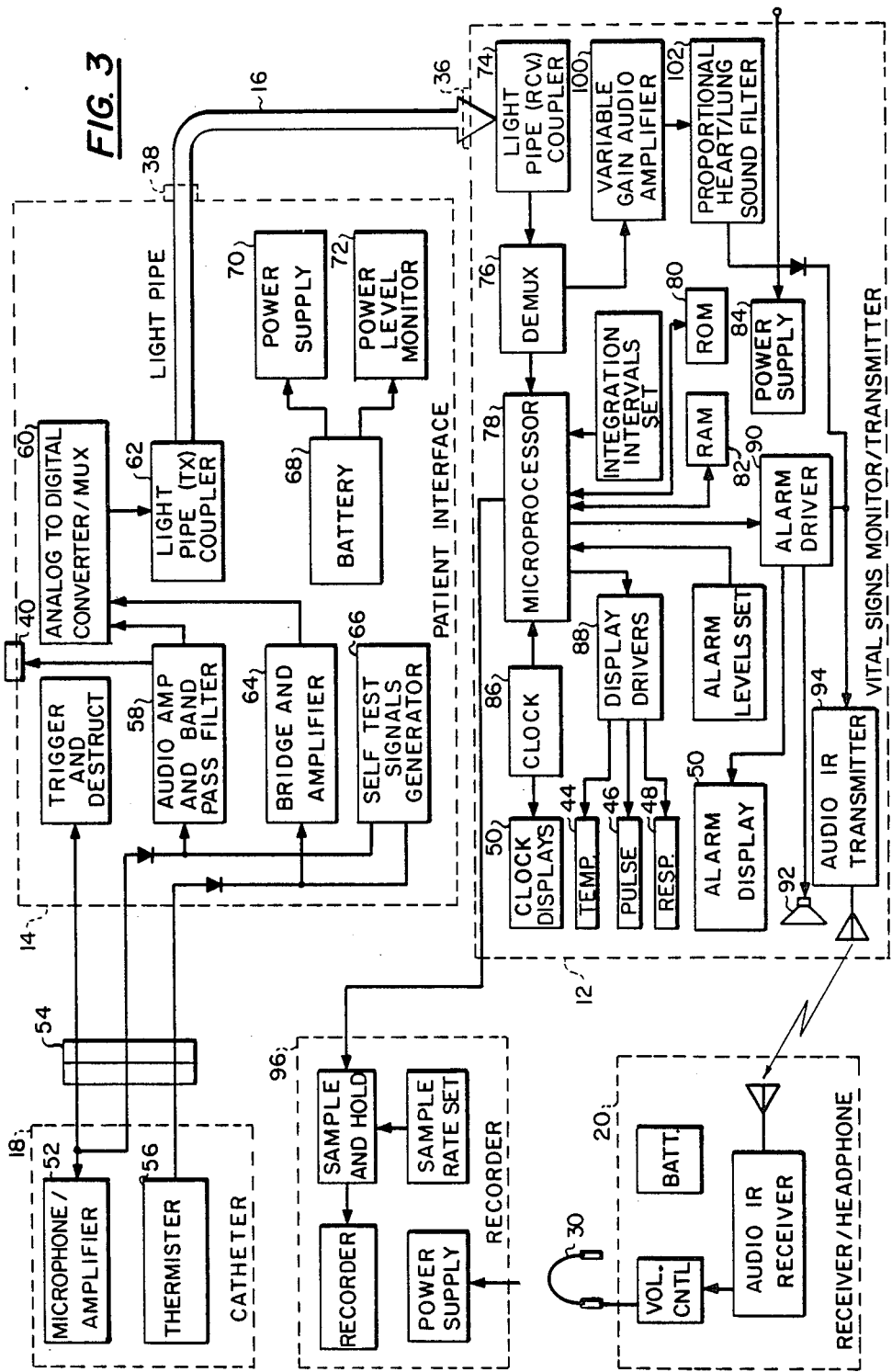
FIG. 3 is an electronic block diagram of the system.

Turning to FIG. 3 of the drawing, a schematic illustration of the functional circuit of the system is illustrated. The catheter 18 includes a microphone and pre-amp circuit 52 connected through suitable leads through a connector 54 which connects into the patient interface unit 14. The microphone 52 is adapted to pick up and transmit signals representative of any sounds such as heart and breathing and other sounds within the body. These sounds are later filtered and the heart and breathing sounds selected and monitored by a filtering circuit as will be explained. Temperature respones means such as a thermister 56 is also disposed within the catheter and connected by suitable electric leads to the connector 54.

Referring to the patient interface unit, signals from the microphone are transmitted to an audio amplifier and band pass filter 58 for filtering and selecting the desired sounds such as heart beat and breathing and are then transmitted to the analog to digital converter multiplexer 60 which converts the signals to digital format and then transmits the signal to a light pipe coupler 62 for transmission by way of the optical fiber or light pipe 16 to the monitor/transmitter unit 12.

The signal from the thermister or temperature sensing element 56 is transmitted by suitable electrical conductors through an electrical bridge circuit and amplifier 64 and then to the analog to digital converter multiplexer 60 for transmission via the light coupler and light pipe 16 to the monitor/transmitter unit 12. A self-test signal generator 66 is connected to the circuit for testing the patient interface unit by simulating microphone and thermister signals. Unit power comes from a suitable battery such as a nine volt transistor battery 68 coupled to a power supply 70 and includes a power level monitor 72. Monitoring of the battery power is important in order to insure adequate power for operation of the system.

The signals from the patient interface unit are communicated by means of the fiberoptic cable 16 to the light pipe or optical coupler 74 from which it is transmitted to a demultiplexer 76 and then transmitted to the microprocesor unit 78. The microprocessor unit may be any suitable microprocessor chipset. The preferred microprocessor unit is such as that available from Intel Corporation as a number 8085. This is a four MHz clock rate device.

The microprocessor unit is programmed much like a computer to control and compute the many functions for the system. The microprocessor unit 78 is intercoupled to suitable memory devices such as an EPROM memory chip 80 and a RAM memory chip 82. The microprocessor is programmed as shown in the flow diagrams of FIGS. 5 and 6 for carrying out the functions set forth therein.

A power supply 84 is connected to a main power supply line 24. The microprocessor 78 is programmed to first carry out a test of the hardware of the system and after the system is confirmed to be operational, it monitors and processes the data received from the sensing units and compares the data to reference data either pre-programmed or self-programmed from prior monitoring and activates a suitable alarm system should critical limits be exceeded.

A clock 86, preferably a quartz crystal oscillator, is interfaced with the microprocessor 78 and functions to supply accurate time and elapsed time to the microprocessor unit and to drive clock displays on the LCD 50. The microprocessor functions to control display drivers 88 which function to drive the displays 44, 46 and 48 for the temperature, pulse and respiration rates display indicators. The microprocessor also drives alarm driver 90 for driving the display alarm through the LCD 50 and audible alarms through the audible alarm speaker 92. Similarly, the alarm driver transmits the alarm signals through an audio infrared (IR) transmitter 94 which transmits the signal to the audio receiver unit 20.

A recorder 96 may be connected into the system for receiving and recording signals from the microprocessor. Various recorders may be suitable for this purpose and preferably would include a power supply, a paper or magnetic tape recorder with a sample and hold buffer with a sample rate set function programmed in.

The monitor/transmitter unit also includes a variable gain auto audio amplifier 100 receiving a signal from the demultiplexer 76 which is fed through a proportional heart-lung sound filter 102 for separating the heart and lung sounds and transmitting them to the audio IR transmitter 94.

The controls of the monitoring system incudes means for setting the time intervals during which the microprocessor monitors each input. Similarly, the microprocessor can be programmed to set alarm levels for the various functions.

Figure 4:
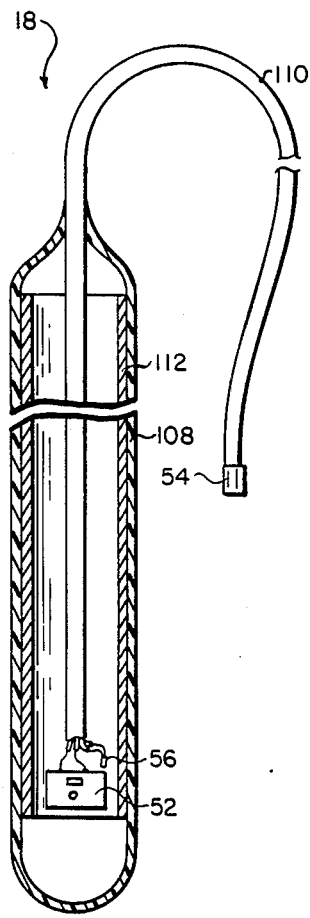
FIG. 4 is an illustration partially in section of the esophageal stethoscope catheter.

Referring to FIG. 4, the esophageal catheter itself 18 comprises an elongated pliable tube or sheath 108 covering or encapsulating the end of a lead cable 110 which contains or houses the leads to the microphone 52 positioned at the closed or digital end of the sheath 108 for protectively covering the thermister and microphone unit. The probe is constructed of the usual material for such probes and is of a convenient size for insertion into the esophagus. The lead 110 is of sufficient length to extend to and couple to the appropriate monitoring equipment.

Figure 6:
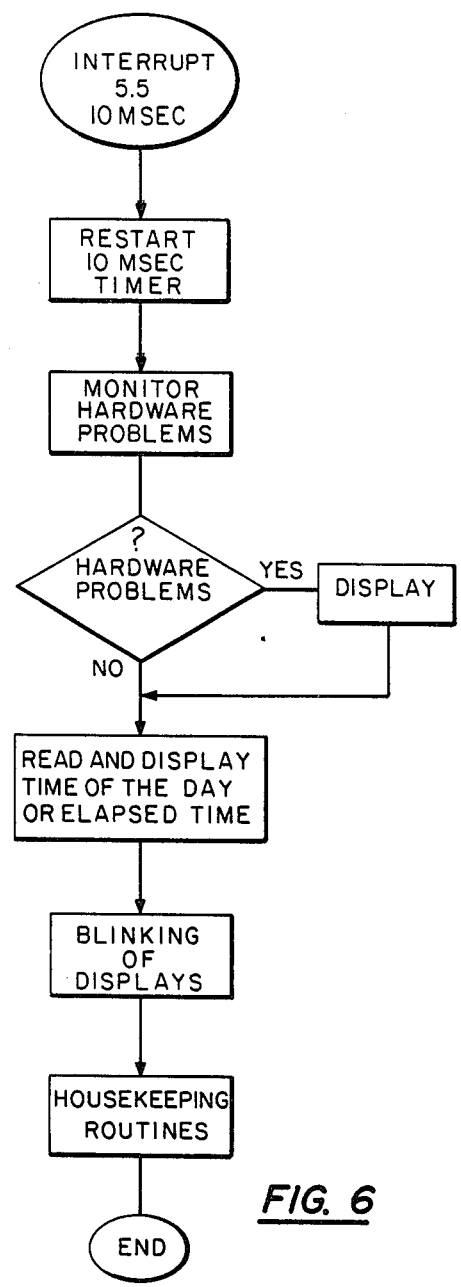
FIG. 6 is a flow chart depicting a typical selfmonitoring routine of the system.
Figure 5:
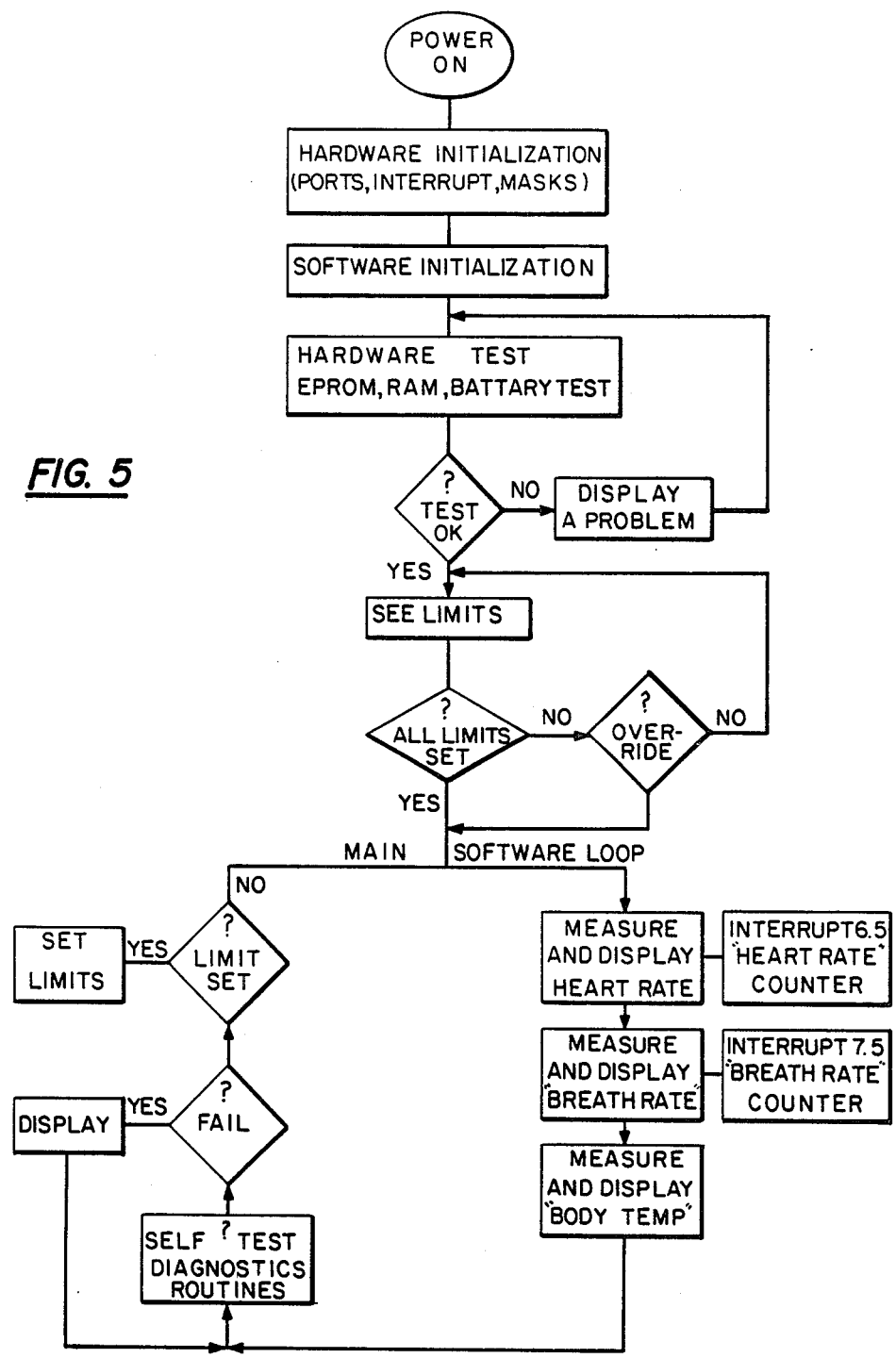
FIG. 5 is a flow chart depicting typical operation of the system.

The system is programmed in accordance with the programmed flow diagrams of FIGS. 5 and 6 to automatically enter into a test mode for testing the various components of the system then go into a set limits mode to permit the limits of the various functions to be set and thereafter go into the monitoring mode for measuring and displaying heart rate, breath rate and body temperature and compare these values with reference or alarm set limit values. Critical deviations from the reference rates signals the microprocessor to drive a suitable auido or visual alarm.

Figure 2:
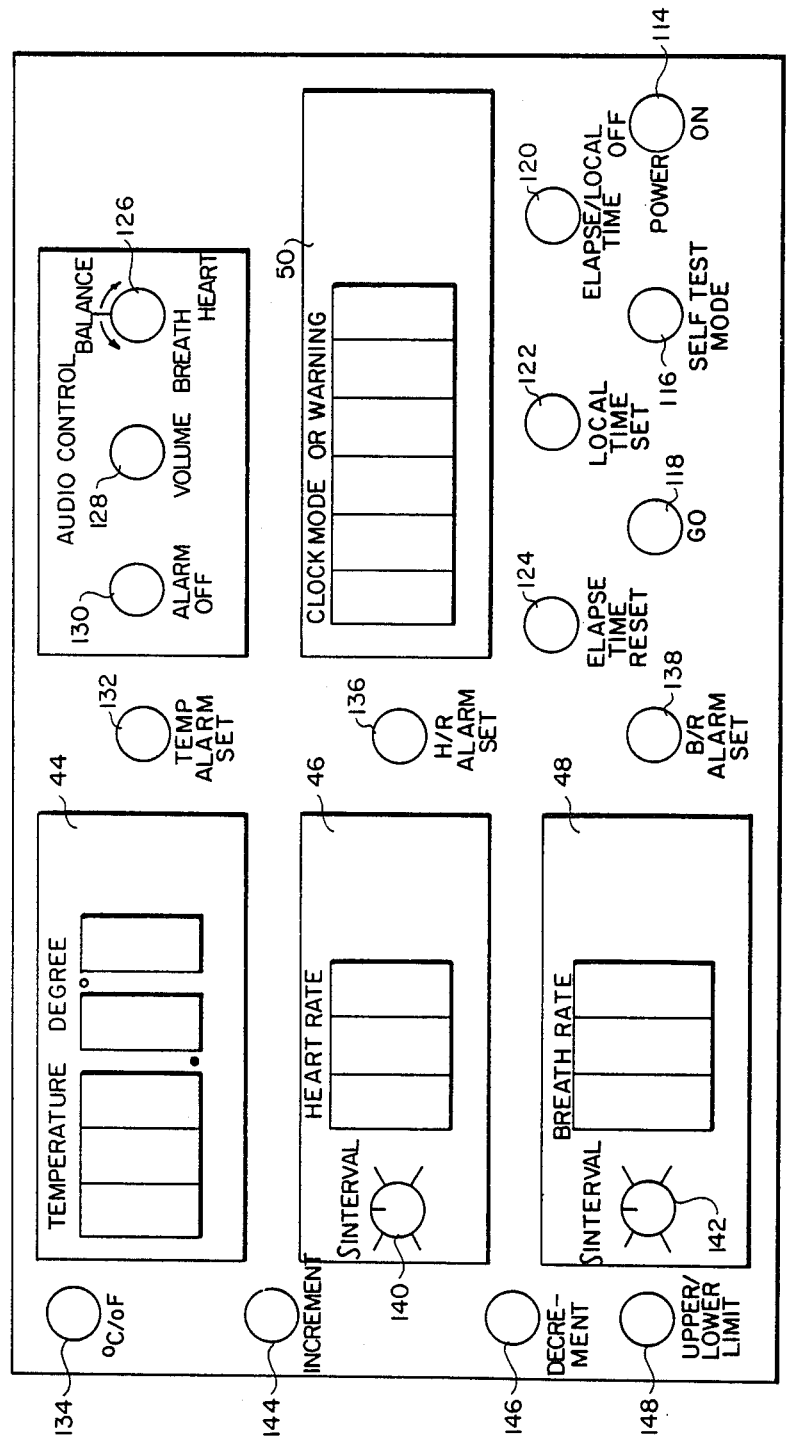
FIG. 2 is a plane view of the control panel of the monitoring system.

In operation the power on switch 114 on the main control panel as shown in FIG. 2 is activated powering up the unit. As the unit is powered on, the various self-test mode routine is initiated and the various components functions are checked. During the self-test mode, the testing of the system progresses with displays of mode test conditions, etc. being displayed by the display 50. A push button switch 118 activates the system to go into the operational monitoring mode after the systems have been checked and determined to be functional. Various timing modes selection controls 120 select elapsed or local time with a control 122 for setting local time and a control 124 for resetting elapsed time. The time indicator LCD module 50 displays and indicates, when in the clock mode, whether elapsed time or local time is being displayed by the letters "E" or "L" in the last LCD.

The audio control includes a balance control 126 for selecting either heart or breath rate or both as would be selected from the central position as indicated. Volume control 128 permits adjustment of the audio volume for the audio signal indicator which may be a beeper, buzzer, horn or the like. An alarm off control 130 permits temporary disconnect of the alarm from the system. a temerature alarm control 132 permits setting of the temperature or alarm limit with a Centrigrade/Fahrenheit selector control 134 for selecting the temperature scale.

Mode indications are displayed by the alpha-numeric LCD display 50 which consists of six alpha-numericals LCD's. When the power is first turned on by activation of switch 114 alpha-numeric LCD module will automatically indicate "TEST" which represents self-test mode and will cycle to limits as programmed which then represents the alarm set mode if no failure exists in the system. Each item of the system will be listed in display 50 as it is being tested as follows: ROM, RAM, BUZZER, TEMP, BREATH, HEART, CATHETER, and BATTERY. If the item being tested is faulty, the display will flash and the audible alarm will be sounded until the faulty item is corrected. The monitor can go no further until the faulty item has been fixed. When the test has been completed, the display will read "TST OK".

If limits are not programmed in for the parameters, the system will default to normal parameter, e.g. 37.0 degrees Centrigrade (or 98.6 degrees Fahrenheit), 70#/min., 17#/min. When the monitor has then proceeded to the operate mode, no mode indication will be displayed on the alpha-numeric LCD module 50 but instead elapsed time will be displayed which starts from the time the monitor enters operate mode with a display form "HH: MME".

The elapsed time clock can be reset to "00:00E" at any time by pressing the elapsed time reset button 124. Elapsed/local time push button is used to toggle the clock display from elapsed time to local time or vice versa. Warning messages will also be indicated by the alphanumeric LCD module 50 which will be discussed later.

Operator selected upper and lower limits for each of the three major parameters are capable of being entered into monitor by selection of the parameter by push buttons 132, 136 and 138.

The limit to be adjusted is selected by button 148 and increased or decreased by buttons 144 and 146. Whenever a measured value exceeds a set limit value for a period of time exceeding the set interval which intervals are selected by interval selectors 140 and 142, the monitor provides visual flashing of the corresponding parameter display on the LCD display 50 and auditory signals such as a warning from the loud speaker 92 and the ear piece 30. Rotary switch 140 provides the operator with four selectable averaging time intervals for heart rate in 8 second increments from 6 to 30 seconds. Breath rate interval selector switch 142 provides the operator with four selectable averaging time intervals in 35 second increments from 15 to 120 seconds. The auditory alarm signal can be stopped by pressing the alarm off button 130 but visual signals cannot be shut off. However, if another measured parameter exceeds a set limit or the measured parameter which previously had caused alarm returned to its setting boundary for a certain period and then exceeds the limit again, the buzzer will turn on again.

In setting the upper and lower limits of the parameters control increment and decrement buttons 144 and 146 are utilized to increase or decrease the selected set parameter during the alarm lever set mode. Upper and lower limits may be checked by control button 148 for each of the selected parameters.

The catheter is provided with a self-destruct circuit which prevents the catheter from being reused as a safety precaution. Due to the potential damage to the sensitive elements of the catheter by sterilization, it is desirable that the unit not be reused. A self-destruct circuit is built into the system as shown in FIG. 7 which results in a destruction of the amplifier circuit for the sound sensing system of the catheter. With specific reference to FIG. 7, the connector coupling 54 is provided with five leads including the main leads of the microphone amplifier circuit and including a short pin connector 150 connecting to the female pin connector 152. A destruct circuit includes a switch 154 which in its normal mode as shown in FIG. 7 connects the microphone and amplifier to the audio amplifier circuit of the patient interface unit. Upon beginning of the disconnect of the cable, in 150 first disengages from socket 52 breaking the open circuit sense and switch circuit 156 which shifts switch 154 to the destruct position for connection into the destruct circuit including a capacitor 158 connected by conductors 160 and 162 to the power supply and is charged with an instantaneous high voltage. Upon switching the switch 54 to the destruct mode the high voltage charge from the capacitor 158 is fed through the amplifier 53 destroying the amplifier. This disables the amplifier circuit and the sound sensing system of esophageal catheter.

While we have illustrated and described our invention by means of specific embodiments, it is to be understood that numerous changes and modifications may be made therein without departing from the spirit and scope of the invention as defined in the appended claims.

We claim:

1. A patient vital signs monitoring system comprising:
   an elongated esophageal catheter having a near end and a closed distal end for placement in a patient's esophagus;
   temperature sensing means in the said catheter for sensing temperature and generating a first electrical signal corrsponding thereto;
   sound sensing means mounted in the said catheter for generating a second electrical signal corresponding to both heart sounds and breathing sounds;
   amplifying means in said catheter for amplifying said second electrical signal;
   conductor means connected to said temperature sensing means and said sound sensing means for conducting said signals away from the patient's body;
   a remotely located monitoring unit connected to said conductor means for receiving said first and second signals and processing said first and second signals, including separating said seond signal into heart sound signals and breathing sound signals;
   said monitoring unit comprising wireless IR transmitting means for transmitting said heart sound signals and said breathing sound signals; and
   a remote portable IR receiving means worn on an opeator's body for receiving and reproducing said sound signals for enabling remote monitoring of said heart sounds and said breathing sounds.

2. The monitoring system of claim 1 including means for electrically isolating said catheter from said monitor unit.

3. The monitoring system of claim 1 including programmable means for establishing a reference temperature; and
   temperature alarm means for providing an alarm signal in response to a critical deviation of the temperature sensed from said reference temperature.

4. The monitoring system of claim 3 wherein said alarm signal is audible.

5. The monitoring system of claim 1 comprising:
   programmable means for establishing a reference heart sound, and heart sound alarm means for providing an alarm signal in response to a deviation in said heart sound from said reference heart sound.

6. The monitoring system of claim 5 wherein said alarm signal is audible.

7. The monitoring system of claim 1 comprising;
   programmable means for establishing a reference breathing sound, and breathing sound alarm means for providing an alarm signal in response to a critical deviation of said breathing sound from said reference sound.

8. The monitoring system of claim 1 comprising programmed means for automatically testing all components of said monitoring system.

9. The monitoring system of claim 8 including display means for displaying information as to the present mode of the monitoring system unit and for indicating each component and its condition as it is being tested.

10. The monitoring system of claim 9 wherein said display means includes a separate simultaneous visual display of temperature, heart rate, breathing rate, and time.

11. The monitoring system of claim 10 wherein said display means includes a separate LCD module for each parameter.

12. The monitoring system of claim 11 wherein said LCD module for displaying time is an alpha-numeric module.

13. The monitoring system of claim 1 including a patient interface unit separate from said signal monitoring and processing means;
   said esophageal catheter is detachably connectable to said patient interface unit; and
   said patient interface unit includes means for monitoring breath and heart sounds.

14. The monitoring system of claim 13 including means for establishing upper and lower limits for each of the parameters of temperature, heart rate, and breath rate.

15. A patient vital signs monitoring system comprising:
   an elongated flexible esophageal catheter having a near end having detachable connecting means and a closed distal end and for placement in a patient's esophagus;
   temperature sensing means in said catheter for sensing temperature and generating a first electrical signal corresponding thereto;
   a single sound sensing means in said catheter for sensing heart sounds and breath sounds and generating a second electrical signal corresponding to said sounds;
   amplifying means in said catheter for amplifying said second electrical signals;
   conductor means connected to said temperature sensing means and said sound sensing means for conducting said signals away from a patient's body;
   a remote monitoring unit connected to said conductor means for receiving and processing said first and second electrical signals and separating said second signal for separately determining patient heart and respiration rate and comparing said rates to predetermined reference rates, said monitoring unit including alarm means responsive to a predetermined critical difference between said compared rates for generating an alarm signal, temperature signal processing means for comparing said temperature signal to a predetermined reference signal, temperature alarm means responsive to a critical difference between said temperature signal and said reference signal for generating a temperature alarm signal;

an infrared transmitter for transmitting said heart sound signals and said breathing sound signals; and a remote portable infrared receiver worn by an operator for receiving and reproducing said sound signals for enabling remote monitoring of said heart sounds and said breathing sounds.

16. The monitoring system of claim 15 including means for electrically isolating said catheter from said monitor unit.

17. The monitoring system of claim 16 including a patient interface unit separate from said signal monitoring and processing means;

said esophageal catheter is detachably connectable to said patient interface unit; and said patient interface unit includes means for monitoring breath and heart sounds.

18. A remote portable patient vital signs monitoring system comprising:

an elongated esophageal catheter having a near end detachably connectable to a remote monitoring unit and a closed distal end for insertion into the esophagus of a patient;

temperature sensing means in the said catheter for sensing a temperature and generating a first electrical signal representative of temperature sensed;

sound sensing means mounted in the said catheter for sensing both heart sounds and chest breathing sounds and generating a second electrical signal representative of said sounds;

amplifying means in said catheter for amplifying said second signals;

conductor means connected to said temperature sensing means and said sound sensing means for conducting said signals away from the patient's body;

a remote portable monitoring unit connected to said conductor means, including means for processing said second signal and separating said signal into heart sounds and chest sounds and proving a separate audible representation of heart sounds and breathing sounds, said signal monitoring and processing means responsive to said temperature signal for providing a visual indication of the temperature sensed by said temperature sensing means; pg,27 programmable means for establishing a reference heart sound, and heart sound alarm means for providing an alarm signal in response to a deviation in said heart sound from said reference heart sounds;

programmable means for establishing a reference breathing sound, and breathing sound alarm means for providing an alarm signal in response to a critical deviation of said breathing sound from said reference sound; and said monitoring means comprising an infrared transmitter for converting and transmitting said heart sound signals and said breathing sound signals via infrared waves, and remote portable infrared receiving means worn by an operator for receiving and converting said infrared waves to sound signals for enabling remote monitoring of said heart sounds and said breathing sounds.

19. The monitoring system of claim 18 including means for electrically isolating said catheter from said monitor unit.

20. The monitoring system of claim 19 including a patient interface unit separate from said signal monitoring and processing means;

said esophageal catheter is detachably connectable to said patient interface unit; and said patient interface unit includes means for monitoring breath and heart sounds.

* * * * *